United States Patent [19]
Detty

[11] Patent Number: 5,865,777
[45] Date of Patent: Feb. 2, 1999

[54] GERIATRIC KNEE BRACE

[76] Inventor: Gerald D. Detty, 3911 W. Lambert La., Tucson, Ariz. 85742

[21] Appl. No.: 71,337

[22] Filed: May 1, 1998

[51] Int. Cl.⁶ ....................................................... A61F 5/00
[52] U.S. Cl. .................................. 602/26; 602/63; 602/62
[58] Field of Search .................................. 602/5, 23, 26, 602/60, 61, 62, 63

[56] References Cited

U.S. PATENT DOCUMENTS

| | | |
|---|---|---|
| 3,463,147 | 8/1969 | Stubbs . |
| 3,473,517 | 10/1969 | Spiro ...................................... 602/26 X |
| 3,703,171 | 11/1972 | Schiavitto . |
| 3,804,084 | 4/1974 | Lehman ................................. 602/26 X |
| 3,831,467 | 8/1974 | Moore . |
| 3,934,583 | 1/1976 | Hollingshead et al. . |
| 3,935,858 | 2/1976 | Harroff ...................................... 602/26 |
| 3,945,046 | 3/1976 | Stromgren . |
| 3,970,081 | 7/1976 | Applegate, Jr. . |
| 4,064,874 | 12/1977 | Valin . |
| 4,084,584 | 4/1978 | Detty . |
| 4,090,508 | 5/1978 | Gaylord, Jr. . |
| 4,116,236 | 9/1978 | Albert . |
| 4,250,578 | 2/1981 | Barlow . |
| 4,296,744 | 10/1981 | Palumbo ............................... 602/26 X |
| 4,353,362 | 10/1982 | DeMarco ................................. 602/26 |
| 4,366,813 | 1/1983 | Nelson .................................. 602/26 X |
| 4,370,978 | 2/1983 | Palumbo . |
| 4,378,009 | 3/1983 | Rowley et al. . |
| 4,388,920 | 6/1983 | Hajost et al. ........................... 602/26 X |
| 4,445,505 | 5/1984 | Labour et al. .......................... 602/26 X |
| 4,474,573 | 10/1984 | Detty . |
| 4,476,857 | 10/1984 | Levine . |
| 4,651,722 | 3/1987 | Karczewski . |
| 4,765,318 | 8/1988 | Tranberg et al. . |
| 5,016,621 | 5/1991 | Bender .................................. 602/26 X |
| 5,024,216 | 6/1991 | Shiono .................................. 602/26 X |
| 5,085,210 | 2/1992 | Smith, III . |
| 5,086,761 | 2/1992 | Ingram . |
| 5,139,477 | 8/1992 | Peters . |
| 5,168,577 | 12/1992 | Detty . |
| 5,221,252 | 6/1993 | Caprio, Jr. et al. . |
| 5,334,135 | 8/1994 | Grim et al. . |
| 5,399,153 | 3/1995 | Caprip, Jr. et al. ........................ 602/26 |
| 5,417,676 | 5/1995 | Gauvry ..................................... 602/26 |
| 5,451,201 | 9/1995 | Prengler . |
| 5,472,413 | 12/1995 | Detty . |
| 5,626,557 | 5/1997 | Mann ........................................ 602/26 |
| 5,656,023 | 8/1997 | Caprio, Jr. et al. ........................ 602/63 |

*Primary Examiner*—Linda C.M. Dvorak
*Attorney, Agent, or Firm*—Caesar, Rivise, Bernstein, Cohen & Pokotilow, Ltd.

[57] ABSTRACT

A knee brace for a person, particularly an elderly person. The knee brace made up of a generally planar sheet of elastomeric, e.g., a plush fabric-covered neoprene, material and has a pair of adjustment straps secured to it. The sheet has a central portion having a longitudinal axis, a first side disposed laterally from the axis and from which an intermediate mounting tab projects and a second side disposed laterally from the axis opposite the first side and from which an upper and a lower mounting tab project. The upper tab includes a free end portion in the form of a VELCRO® multi-hook connector. The intermediate tab is similarly constructed, as is the lower tab. The central portion of the brace is arranged to be mounted on the person's knee so that the longitudinal axis is over the person's patella. The upper tab is arranged to be stretched and wrapped around the posterior of the person's thigh so that it's VELCRO® multi-hook connector releasably engages the plush fabric of the central portion contiguous the said first side to hold it in place. The lower tab is arranged to be stretched and wrapped around the posterior the person's calf so that it's VELCRO® multi-hook connector releasably engages the plush fabric of the central portion contiguous with the first side to hold it in place. The intermediate tab is arranged to be stretched and wrapped around the posterior the person's knee so that it's VELCRO® multi-hook connector releasably engages the plush fabric of the portion contiguous with the second side to hold it in place. One of the adjustment straps is an inelastic member which is located on the central portion of the brace above the person's patella to adjust the tightness of the brace on the person's thigh, while the other of the adjustment straps is similarly constructed and is located on said central portion of the brace below the person's patella to adjust the tightness of the brace on the person's calf.

13 Claims, 3 Drawing Sheets

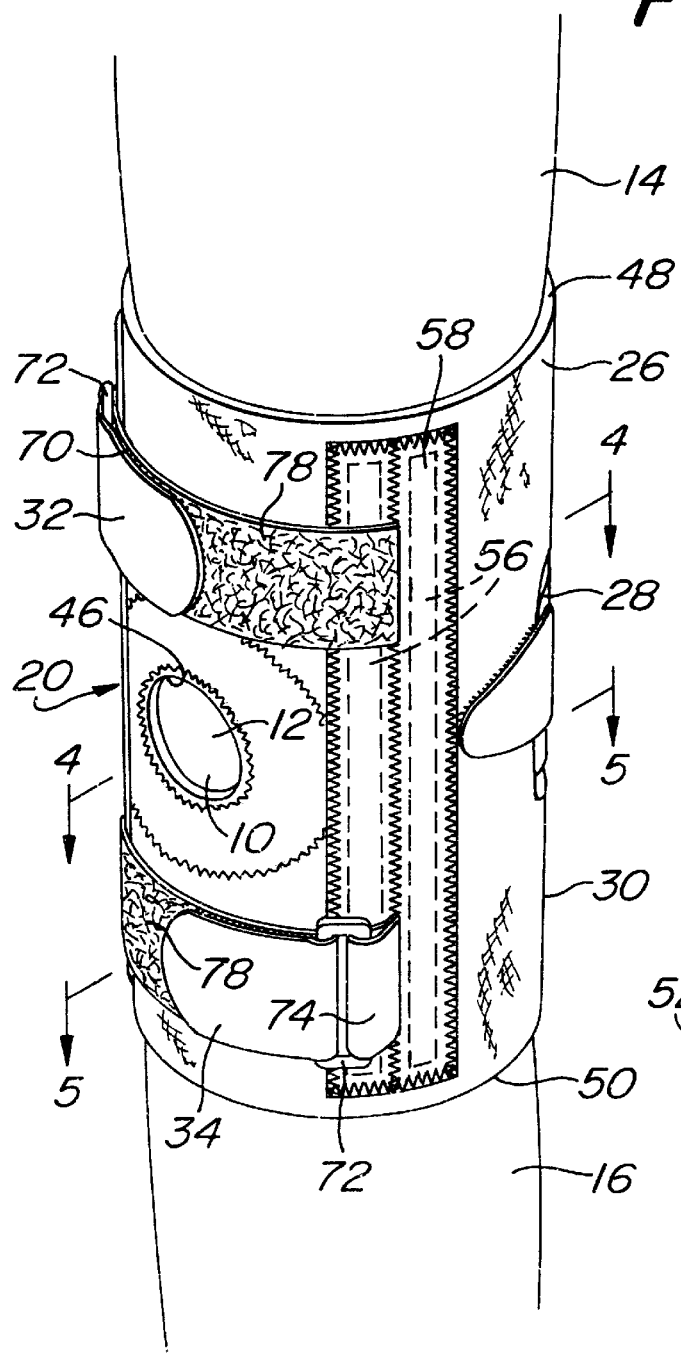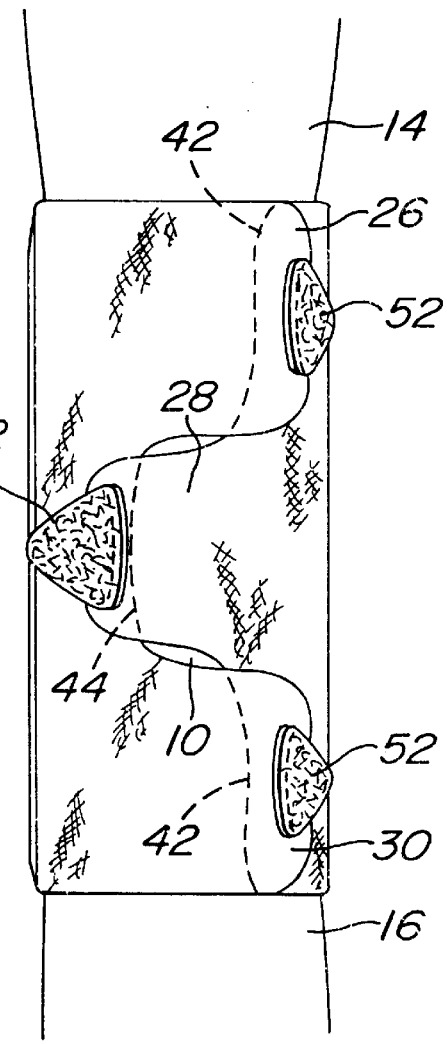

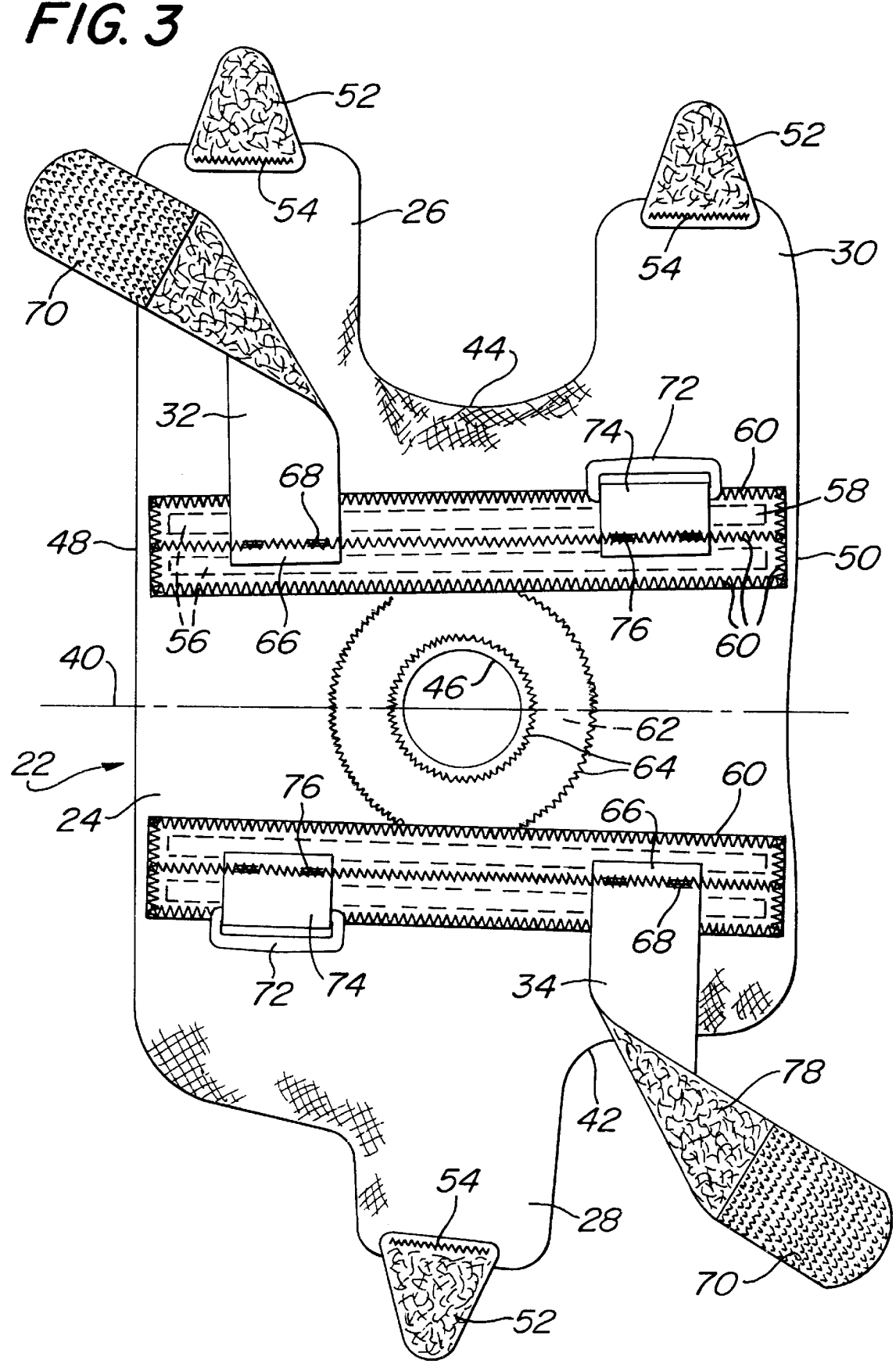

GERIATRIC KNEE BRACE

BACKGROUND OF THE INVENTION

This invention relates generally to knee braces and more particularly to knee braces for use by the elderly.

Various knee braces in the form of elastic sleeves are commercially available and/or are disclosed in the patent literature for use on a person's knee to stabilize the joint and patella. Examples of such braces are disclosed in U.S. Pat. Nos.: 3,703,171 (Schiavitto), 3,934,583 (Hollingshead), 3,945,046 (Stromgren), 3,970,081 (Applegate), 4,064,874 (Valin), 4,084,584 (Detty), 4,116,236 (Albert), 4,250,578 (Barlow), 4,296,744 (Palumbo), 4,353,362 (DeMarco), 4,366,813 (Nelson), 4,370,978 (Palumbo), 4,474,573 (Detty), 4,476,857 (Levine), 4,765,318 (Per Tranberg et al.), 5,085,210 (Smith), 5,139,477 (Peters), 5,168,577 (Detty), and 5,334,135 (Grim). While such sleeves are generally suitable for their intended purposes, a large segment of the population, namely, the elderly, may be incapable of adequately using such braces since they no longer have sufficient hand strength and/or dexterity to pull the sleeve onto their knee.

Various wrap-around knee braces are commercially available and/or disclosed in the patent literature. Examples of such braces are disclosed in U.S. Pat. Nos.: 3,463,147 (Stubbs), 3,831,467 (Moore), 4,090,508 (Gaylord, Jr.), 4,651,722 (Karczewski), 4,378,009 (Rowley et al.), 5,024,216 (Hiono), 5,086,761 (Ingram), 5,221,252 (Caprio et al.), 5,399,153 (Caprio et al.), 5,451,201 (Prengler), and 5,472,413 (Detty).

While the aforementioned wrap-around braces are suitable for their intended purposes, and in some cases may be easier to apply than elastic sleeve braces, these wrap-around braces still leave something to be desired from the standpoint of applicability for the geriatric market.

OBJECTS OF THE INVENTION

Accordingly, it is a general object of this invention to provide an knee brace which overcomes the disadvantages of the prior art.

It is a further object of this invention to provide a wrap around knee brace which is easy to apply and remove.

It is a further object of this invention to provide a wrap around knee brace which is comfortable to wear.

It is a further object of this invention to provide a wrap around knee brace which provides good support for the knee structures.

It is a further object of this invention to provide a wrap around knee brace which serves to stabilize the knee joint and the patella.

It is a further object of this invention to provide a wrap around knee brace which when mounted is resistant to slippage, e.g., "riding-up" or sliding down.

It is a further object of this invention to provide a wrap around knee brace which does not bunch up in the back of the knee.

It is still a further object of this invention to provide a wrap around knee brace, which when mounted in place acts like a sleeve brace.

SUMMARY OF THE INVENTION

These and other objects of this invention are achieved by providing a knee brace for a person, e.g., an elderly person. The knee brace is formed of a generally planar sheet of elastomeric, e.g., fabric coated neoprene, material and has a pair of adjustment straps secured thereto. The elastomeric sheet comprises a central portion having a longitudinal axis, a first side disposed laterally from that axis and from which an intermediate mounting tab projects and a second side disposed laterally from that axis opposite the first side and from which an upper and a lower mounting tab project. The upper tab of the brace includes a free end portion in the form of an upper releasably securable connector. The intermediate tab includes a free end portion in the form of an intermediate releasably securable connector. The lower tab includes a free end portion in the form of a lower releasably securable connector.

The central portion of the brace is arranged to be disposed on the person's knee so that the longitudinal axis is disposed over the person's patella. The upper tab of the brace is arranged to be stretched and wrapped around the posterior of the person's thigh so that it's upper releasably securable connector releasably engages the central portion of the brace contiguous with the first side. In a similar manner, the lower tab is arranged to be stretched and wrapped around the posterior the person's calf so that its lower releasably securable connector releasably engages the central portion of the brace contiguous with the first side. The intermediate tab is arranged to be stretched and wrapped around the posterior of the knee in the opposite direction so that it's intermediate releasably securable connector releasably engages the central portion of the brace contiguous with the second side.

One of the pair of adjustment straps is located on the central portion of the brace above the person's patella to adjust the tightness of the brace on the person's thigh, while the other of those straps is located on the central portion of the brace below the person's patella to adjust the tightness of the brace on the person's calf.

In accordance with one aspect of the invention the adjustment straps are inelastic and are continuously adjustable.

In accordance with another aspect of the invention the brace may include an opening in the central portion on the longitudinal axis to receive the person's patella and/or include stays or other members on either side of the longitudinal axis.

DESCRIPTION OF THE DRAWING

Other objects and many attendant features of this invention will become readily appreciated as the same becomes better understood by reference to the following detailed description when considered in connection with the accompanying drawing wherein:

FIG. 1 is an isometric view of the knee brace of this invention shown in place on the knee of a person;

FIG. 2 is a reduced elevational view showing the knee brace from the rear of the knee;

FIG. 3 is an enlarged plan view of the brace shown in FIG. 1, but in its natural, e.g., flat, state ready for application to the knee of the person;

DETAILED DESCRIPTION OF THE PREFERRED EMBODIMENTS

Figure 4:
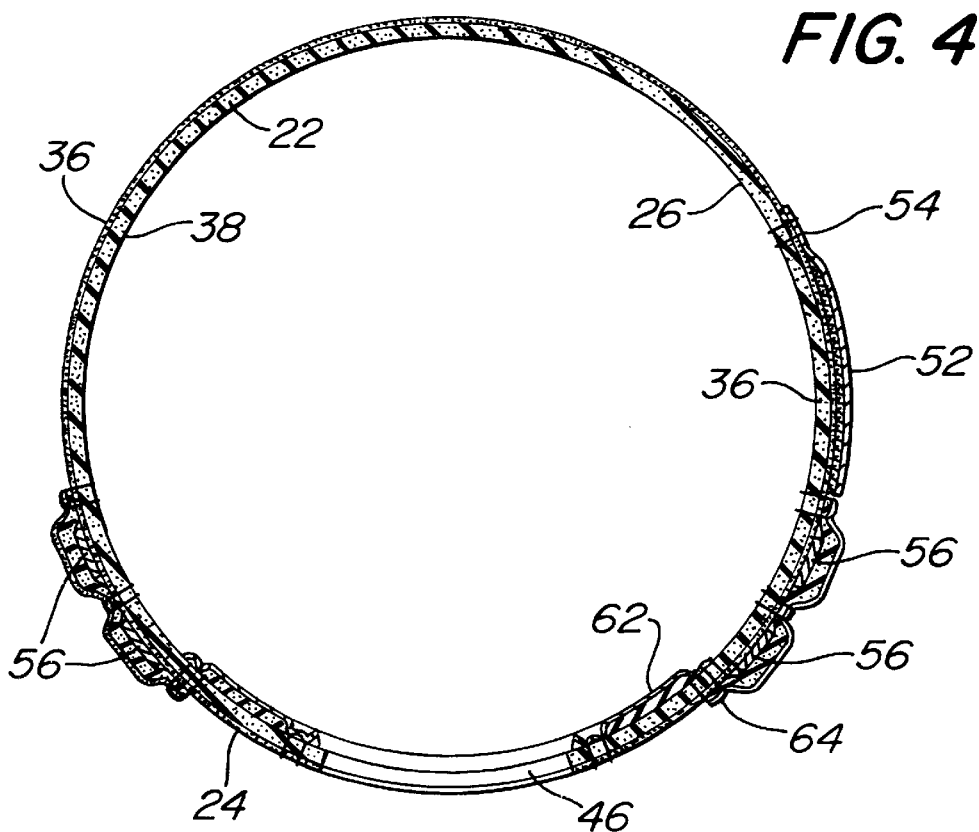
FIG. 4 is an enlarged sectional view taken along line 4—4 of FIG. 1.

Referring now to the drawing where like reference numerals refer to like parts there is shown at 20 in FIG. 1 a brace constructed in accordance with this invention for use on the knee 10 of a person, and particularly an elderly person. As best seen in FIG. 3, the knee brace 20 is a unitary, planar sheet 22 of flexible material (to be described later) which is arranged to be wrapped around the knee of a person. The planar sheet includes a central portion 24 and three mounting tabs, 26, 28, and 30, to be described later, which are used to mount the brace on the person's knee 10. A pair of adjustment straps, 32 and 34, also to be described later, are secured to the brace to enable the wearer to tighten of the brace on his/her knee.

The planar sheet is preferably formed of a blank of elastomeric material which is die cut into a predetermined shape to form the central portion 24 and the mounting tabs 26, 28, and 30. The material forming the sheet is most preferably a plush fabric-coated neoprene. In particular the sheet has an outer surface to which a fabric layer 36 (FIGS. 4 and 5) is secured, e.g., glued, to form the outer surface of the brace. The inner surface of the sheet has a fabric layer 38 secured, e.g., glued, to it to form the inner surface of the brace. The neoprene sheet is of a substantial thickness, e.g. approximately 4 mm. thick, to provide cushioning, support and thermal retention. In accordance with the preferred aspect of the invention, the fabric 36 forming the outer surface of the brace is tufted or plush, e.g., is a UBL (unbroken loop) fabric, compatible with VELCRO® multi-hook fastening components so that it can act as the multiple loop fastening component of a VELCRO® fastening system to facilitate the mounting of the brace on the person's knee (as will be described later). The fabric layer 38 forming the inner surface of the brace is selected to be comfortable and non-chafing, e.g., is a smooth nylon tricot.

The central portion 24 of the neoprene sheet is of a generally rectangular shape having a longitudinal central or mid-line axis 40, a first lateral side 42 located on one side of the axis 40 and a second lateral side 44 located on the opposite side of the axis 40. A central opening 46 for receiving the wearer's patella 12 (FIG. 1) is located in approximately the center of the central portion on the axis 40.

The mounting tab 26, hereinafter referred to as the upper mounting tab, constitutes a generally rectangular projection of the sheet of neoprene material 22 extending from the second lateral side 44 perpendicular to the longitudinal axis 40 and contiguous with the top edge 48 of the brace. The mounting tab 30, hereinafter referred to as the lower mounting tab, constitutes a generally rectangular projection of the sheet of the neoprene material 22 also extending from the second lateral side 44 perpendicular to the longitudinal axis 40 and contiguous with the bottom edge 50 of the brace. Thus, both the upper and lower mounting tabs extend from the same side of the brace and are arranged to be wrapped about respective portions of the wearer's leg, i.e., the thigh region 14 (FIG. 1) and the calf region 16 (FIG. 1), respectively, from the same direction.

The lower mounting tab 30 does not extend as far outward from the longitudinal axis 40 as the upper mounting tab 26, since the lower tab 30 is arranged to be stretched and wrapped around the wearer's calf region 16, whereas the upper tab 26 is arranged to be stretched and wrapped around the wearer's thigh region 14 (a larger diameter structure than the calf region). In a similar manner, the portion of the first lateral side 42 of the brace located opposite to the upper mounting tab 26 extends further from the central longitudinal axis 40 than the portion of that side located opposite to the lower mounting tab 30, in order to accommodate the larger diameter thigh region.

The mounting tab 28, hereinafter referred to as the intermediate mounting tab, also constitutes a generally rectangular projection of the sheet of neoprene material 22, but it extends from the first lateral side 42 of the brace perpendicular to the longitudinal axis 40 and between the upper and lower mounting tabs 26 and 30, respectively. The intermediate mounting tab 28 is arranged to be stretched and wrapped around the back of the person's knee in the opposite direction than the upper and lower tabs 26 and 30, respectively, as best seen in FIG. 2. The intermediate mounting tab 28 extends approximately the same distance from the central longitudinal axis 40 as does the lower mounting tab 30 (albeit from the opposite side of the brace). Moreover, the width of the intermediate mounting tab 28 is such that it may fit within the space between the upper and lower mounting tabs on the second side of the brace with minimal, if any, overlapping, when the brace is in place on the wearer's knee. This feature, as best seen in FIG. 2, is of considerable importance to minimize any tendency for the brace to bunch up behind the knee, particularly when the knee is bent.

As can be seen in FIGS. 1 and 2 the upper mounting tab 26 is arranged to be stretched and wrapped about a portion of the wearer's thigh region 14 immediately over his/her knee 10, while the lower mounting tab 30 is arranged to be stretched and wrapped around the wearer's calf region 16 immediately below the knee 10. To secure the upper mounting tab 26 in place after it has been wrapped around the back of the thigh region, a connector is provided on the free end of the tab. In particular, the tab includes a free end portion in the form of a generally triangular ear 52 whose inner surface is a multi-hook-type VELCRO® fastener. As can best be seen in FIG. 3, the ear 52 is secured to end of the upper mounting tab 26 by plural stitches 54. The lower mounting tab 30 is similarly constructed to include a triangular ear whose inner surface is a hook-type VELCRO® fastener and which is secured to the end of that tab by plural stitches 54.

When the upper mounting tab 26 is stretched and wrapped around the rear portion of the wearer's thigh, the multiple hooks of the Velcro® ear 52 of the upper mounting tab 26 releasably engage the plush fabric 38 of brace slightly below the brace's top edge 48 and adjacent it's first lateral side 42. This action releasably secures the upper mounting tab 26 to the first side 42 of the brace by encircling the thigh region of the wearer's leg. As will be appreciated by those skilled in the art, since the brace is elastic, the amount of overlap of the upper mounting tab 26 on the side 42 of the brace is adjustable to accommodate thigh regions of various sizes. The lower mounting tab 30 is wrapped around the wearer's calf region 16 in the same manner as the upper mounting tab, so that the lower mounting tab's ear 52 releasably engages the plush fabric 28 of the brace slightly above the brace's bottom edge 50 and adjacent it's first lateral side 42, to releasably secure the lower mounting tab 30 to that side of the brace. The amount of overlap of the tab 30 on the first side 42 of the brace is, thus, also adjustable to accommodate calf regions of various sizes.

The intermediate mounting tab 28 is stretched and wrapped in the opposite direction behind the knee as the upper and lower mounting tabs. Accordingly, the multiple hooks of the intermediate tab's Velcro® ear 52 releasably engage the plush fabric 28 of brace contiguous with brace's second lateral side 44 between the upper and lower mounting tabs 26 and 30, respectively. This action releasably secures the intermediate mounting tab 28 to the second side 44 of the brace, with the amount of overlap also being adjustable to accommodate knee joints of various sizes.

In accordance with one preferred aspect of this invention the outer surface of each of the ears 52 is in the form of a plush fabric, e.g., a UBL fabric compatible with a hook type VELCRO® fastener, so that the hook like components of any of the other ears 52 can be releasably secured to that surface in lieu of or in addition to securement to the plush outer surface 36 of the brace itself when the brace is in place. This feature enables each of the mounting tabs to be precisely located as desired to enable the brace to conform to the particular anatomy of the wearer. The ears 52 having the multi-hook inner surface and UBL multi-loop outer surface may be made from components sold under the trademark VELCRO ONE-WRAP TABS. Other similar commercially available products can be used as well.

As should be appreciated by those skilled in the art, since the upper and lower mounting tabs are wrapped in one direction about the rear of the wearer's leg, while the intermediate mounting tab is wrapped in the opposite direction, the tension provided by the mounting of the brace on the leg tends to be equalized on the knee.

As mentioned earlier the center of the central portion of the brace includes an opening or a hole 46 to accommodate the patella 12, when the brace is in place on the knee. If desired, the brace need not include such an opening. One or more stays or other reinforcing components may be provided as part of the brace, if desired. In the embodiment shown herein the brace includes four such reinforcing stays 56 mounted in the central portion 24 of the brace 20. Each stay 56 is an elongated strip of resilient material, e.g., a thin plastic strip or a flattened coil of aluminum or other metal, to provide additional stability to the knee and/or to keep the brace from collapsing on the knee when the knee is flexed. In the exemplary embodiment shown herein, a first pair of stays 56 (FIGS. 1, 3, 4, and 5) are mounted on the front surface of the central portion 24 of the brace 20 on one side of the central longitudinal axis 40 to extend parallel thereto. The first pair of stays 56 is held in place on the central portion by a cover strip 58 formed of the same material as the brace. The cover strip is disposed over the stays and is secured in place by lines of stitches 60 extending along the periphery of the cover strip and down its center between the pair of stays. The other pair of stays 56 are identical to the first pair of stays 56, and are mounted in an identical manner, except that they are located in the central portion 24 of the brace 20 on opposite the side of the central longitudinal axis as the first pair of stays.

It must be pointed out at this juncture that the use of one or more stays, like stays 56, in the brace 20 is optional. Moreover, the brace may optionally include one or more other structural components, e.g., hinges, plates, etc., depending upon the particular function desired to be provided by such component(s). Those optional components may be built into the brace or arranged for releasable securement thereto. For example, with respect to the latter case and in accordance with the exemplary embodiment shown herein, a planar sheet of any suitable plush UBL material, e.g., a fabric covered foam is provided as part of the brace. This sheet is in the form of a ring 62 which is secured by plural stitch lines 64 onto the inner surface 38 of the brace 20 about the periphery of the patella-receiving opening 46. The ring 62 serves as a mount for an optional patella stabilizer or patella control device (not shown). One such patella control device is a horseshoe shaped or C-shaped member (not shown) which includes a multi-hook component of a VELCRO® fastening system fixedly secured to it to enable it to be releasably mounted on the ring 62 within the brace at various orientations with respect to the patella opening 46. In particular, the multi-hook component of the VELCRO® fastener on the patella control device can be brought into engagement with the plush UBL outer surface of the ring 62 at any angular orientation with respect to the center of the ring 62 to releasably mount the patella control device thereon. When so mounted the patella control device will serve to restrict movement of the patella in the desired direction(s), thereby stabilizing the patella.

As mentioned earlier, the brace includes adjustment straps 32 and 34 to enable the wearer to customize the tension or tightness applied by the brace to the thigh region 14 and the calf region 16, respectively. The two adjustment straps are constructed identically to each other. Thus, in the interest of brevity only the construction of the upper adjustment strap 32 will be described. As can be seen in FIG. 3 the strap 32 basically comprises an elongated flexible web of inelastic fabric, e.g., nylon, having a first end portion 66 fixedly secured by a line of stitches 68 to the outer surface of the central portion 24 of the brace 20 approximately midway between the longitudinal axis 40 and the second side 44 and slightly below the top edge 48. The opposite end of the strap 32 constitutes its free end 70 and its construction will be described later. In a similar manner the first end portion 66 of the lower adjustment strap 34 is fixedly secured by a line of stitches 68 to the outer surface of the central portion of the brace approximately midway between the longitudinal axis 40 and the second side 44 and slightly above the bottom edge 50. In the exemplary embodiment shown herein the upper and lower adjustment straps 32 and 34, respectively, are secured to the central portion of the brace along the central stitch line 60 between the pairs of stays.

The free end portion 70 of each of the adjustment straps 34 and 36 is arranged to be extended through a respective buckle mounted on the brace to tighten the brace around the portion of the leg at which the strap is located. To achieve that end the free end portion 70 of each adjustment strap is in the form of a releasable securable connector (to be described later) which can be extended through the buckle and folded back over itself so that the releasably securable connector is releasably secured to contiguous portions of the strap. This action secures the strap to the buckle to maintain the desired degree of tension on the brace.

Figure 5:
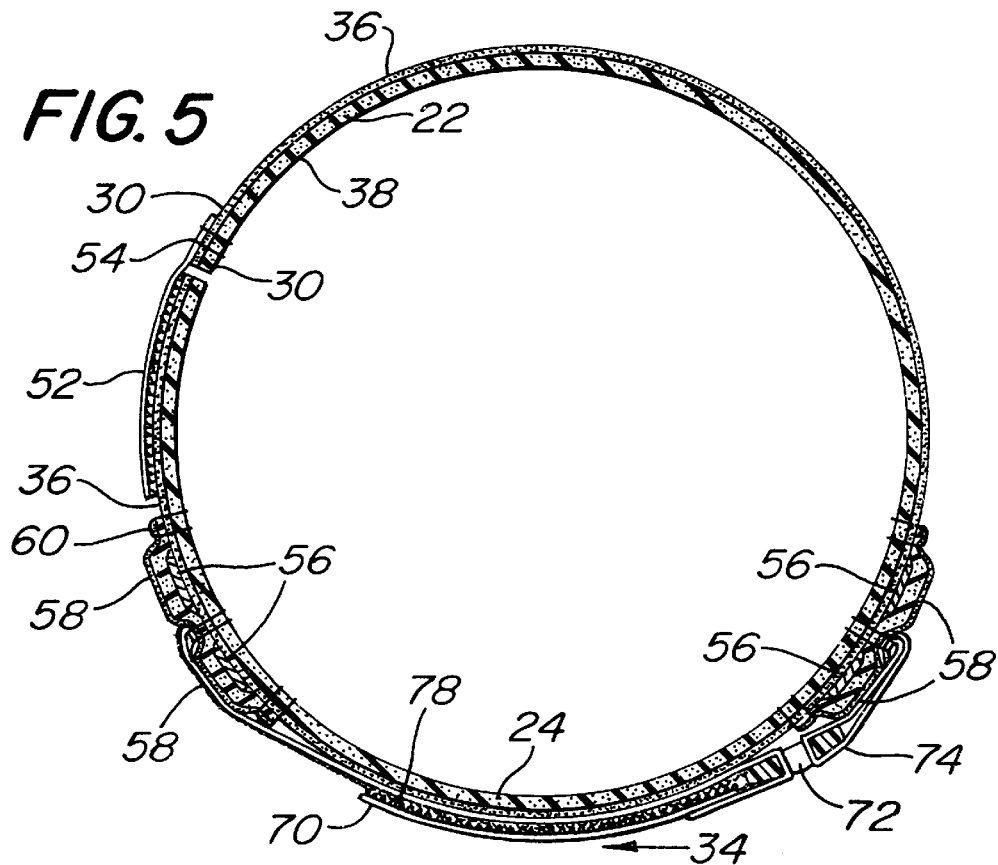
FIG. 5 is an enlarged sectional view taken along line 5—5 of FIG. 1.

Referring now to FIGS. 3 and 5, it can be seen that the buckles are in the form of a pair of rings 72 fixedly secured to the central portion 24 of the brace opposite from the point at which the adjustment straps are fixedly secured thereto. Each buckle 72 is of a generally elongated rectangular shape and includes a central opening for receipt of the free end portion of the associated adjustment strap therethrough. Each buckle is fixedly secured to the brace by a strip of inelastic, e.g., nylon, material 74 extended through the central opening of the buckle and folded back over itself so that its ends meet to form a loop. The ends of the strip forming the loop are secured to the brace by a line of stitches 76. The upper buckle 72 is secured to the central portion of the brace on its outer surface approximately midway between the longitudinal axis 40 and the first side 44 at the same distance below the top edge 48 that the end portion 66 of the upper adjustment strap 32 is connected to the brace. The lower buckle 72 is secured to the central portion of the brace on its outer surface approximately midway between the longitudinal axis 40 and the first side 44 at the same distance above the bottom edge 50 that the end portion 66 of the lower adjustment strap 34 is connected to the brace.

As mentioned earlier each adjustment strap 32 and 34 terminates in a free end portion 70 in the form of a releasably securable connector. In particular, the free end portion 70 comprises a strip of nylon whose outer surface is a multi-hook component of a VELCRO® fastening system. This portion is heat sealed onto the unsecured end of the web of material forming the upper adjustment strap 32. The web of material forming the portion of the adjustment strap between the end portion 66 and the free end 70, is also formed of nylon and has an outer surface in the form of a cooperating component 78, e.g., a plush or multi-loop component, of the VELCRO® fastening system. The two components 70 and 78 of the VELCRO® fastening system of each strap enable the strap to be secured to the associated buckle at whatever tightness the wearer the desires. In particular, to tighten the top of the brace the wearer extends the multi-hook free end portion 70 of the upper adjustment strap 32 across the upper portion of the brace and through the opening in the upper buckle 72. The desired amount of tension can be readily applied by pulling on the free end portion 70 of the upper adjustment strap and folding it back over itself. To maintain that amount of tension all that is required is for the wearer to bring the multi-hook component on the free end 70 of that strap into engagement with the underlying plush component 78 portion of that strap. This action releasably secures those components together, thereby preventing the adjustment strap from loosening in the buckle. The tightening of the lower securement strap 34 is achieved in the same manner.

In order to release either adjustment strap, e.g., to either tighten or loosen that strap, all that is required is to pull on the free end portion 70 of the strap to peel it out from engagement with the underlying component 78 of the strap, thereby enabling the strap to be moved with respect to the buckle 72 to a new tightness setting.

As will be appreciated from the foregoing, the removal of the knee brace 20 can be readily achieved by even persons having very little hand strength and/or dexterity/coordination. In particular, to accomplish that task, all that the user has to do is to grasp the ear 52 of each of the mounting tabs and peel it away from the plush fabric 38 on the surface of the brace to which it is releasably secured. This action releases each ear from connection, thereby freeing the associated mounting tab. When all the tabs are free, the brace can be taken off the knee.

It should be pointed out at this junction that other materials than those described heretofore can be used to make the brace of this invention. For example, elastomeric materials other than neoprene having a tufted fabric covering may be used. Thus, the neoprene may not be covered by any fabric or may be covered by a non-tufted fabric, such as smooth nylon. In the case where the material of the sheet of material forming the brace does not include a plush fabric covering, the outer surface of that sheet should include at least patches of a plush or multi-loop VELCRO® component secured thereto for engagement by the multi-hook VELCRO® component of the ears of the mounting tabs and the multi-hook VELCRO® component of the adjustment straps. In fact, other releasably securable means can be used in lieu of VELCRO® components, if desired. Moreover, in some cases, it may not be desired to use neoprene as the material of the brace. Thus, other elastic materials, with or without cushioning and thermal retention properties may be used for either, if desired. Further still, the central portion 24 and tabs 26–30 need not be a unitary member, i.e., formed of a single piece of material. Thus, one or more of those portions of the brace may be formed of plural pieces which are secured together to form an integral assembly.

As should be appreciated from the foregoing, the braces of the subject invention can be applied to various sized limbs without requiring undue stretching or manipulation. This feature makes it particularly suitable for geriatric applications Moreover, the adjustment straps of the brace provide customized tensioning of the brace above and below the knee, while leaving the patella unconstrained by any strap stretched thereover (as has characterized several prior art knee braces). Moreover, the opposite direction wrapping of the mounting tabs provides increased balance and stability for the brace. Further still, the application of the brace to the joint can be achieved quite easily and simply and does not require complicated wrappings of long straps. All that is required is to pull and stretch the various mounting straps and secure the fastening means. The application of customized tension to the brace is also readily achieved by extending and fastening the adjustment straps across the upper and lower anterior portions of the brace.

Moreover, the construction of the knee brace of this invention is very simple. In this regard it can be readily fabricated from any suitable material(s), e.g., a sheet of fabric covered neoprene. Once fabricated and assembled, the generally flat shape of the brace enables it to be transported and warehoused inexpensively, as compared to the prior art.

Without further elaboration, the foregoing will so fully illustrate my invention, that others may, by applying current or future knowledge, readily adapt the same for use under the various conditions of service.

What is claimed is:

1. A knee brace for a person, said knee brace being formed of a generally planar sheet of elastomeric material and having a pair of adjustment straps secured thereto, said elastomeric sheet comprising a central portion having a longitudinal axis, a first side disposed laterally from said axis and from which an intermediate mounting tab projects and a second side disposed laterally from said axis opposite said first side and from which an upper and a lower mounting tab project, said upper tab including a free end portion in the form of an upper releasably securable connector, said intermediate tab including a free end portion in the form of an intermediate releasably securable connector, said lower tab including a free end portion in the form of a lower releasably securable connector, said central portion of said brace being arranged to be disposed on the person's knee so that said longitudinal axis is disposed over the person's patella, said upper tab being arranged to be stretched and wrapped around the posterior of the person's thigh so that said upper releasably securable connector releasably engages said central portion of said brace contiguous with said first side, said lower tab being arranged to be stretched and wrapped around the posterior of the person's calf so that said lower releasably securable connector releasably engages said central portion of said brace contiguous with said first side, said intermediate tab being arranged to be stretched and wrapped around the posterior of the knee so that said intermediate releasably securable connector releasably engages said central portion of said brace contiguous with said second side, one of said pair of adjustment straps being located on said central portion of said brace and adapted to be positioned above the person's patella in use to adjust the tightness of the brace on the person's thigh, and the other of said pair of adjustment straps being located on said central portion of said brace and adapted to be positioned below the person's patella in use to adjust the tightness of the brace on the person's calf.

2. The knee brace of claim 1 wherein each of said adjustment straps is inelastic.

3. The knee brace of claim 1 wherein each of said adjustment straps is adjustable.

4. The knee brace of claim 3 additionally comprising a first loop member and a second loop member, said first loop member being mounted on said central portion of said brace adjacent said first side and substantially aligned with said upper mounting tab, said one adjustment strap having a first end fixedly secured to said central portion of said brace adjacent said second side and substantially aligned with said upper mounting tab and having a free end arranged to be extended across said central portion of said brace and through said first loop member to tighten said brace on the person's thigh, said second loop member being mounted on said central portion of said brace adjacent said first side and substantially aligned with said lower mounting tab, said other adjustment strap having a first end fixedly secured to said central portion of said brace adjacent said second side and substantially aligned with said lower mounting tab and having a free end arranged to be extended across said central portion of said brace and through said second loop member to tighten said brace on the person's calf.

5. The knee brace of claim 4 wherein the free end of each of said adjustment straps comprises an free end area of one component of a releasable fastening system and another area of a cooperating component of said releasable fastening system, whereupon when said free end of each of said adjustment straps is extended through its associated loop member said free end area component releasably engages said cooperating component to hold the adjustment strap in place extended across said central portion of said brace.

6. The knee brace of claim 1 wherein each of said releasably securable connectors comprises a multi-hook component of a releasable fastening system, and wherein said central portion of said brace includes an outer surface formed of a plush component of a releasable fastening system, whereupon engagement of said multi-hook component to said plush component effects the releasable securement of said connector to said central portion of said brace.

7. The knee brace of claim 1 wherein said elastomeric material comprises neoprene.

8. The knee brace of claim 7 wherein said planar sheet of neoprene has an inner surface and an outer surface, and wherein each of said surfaces is in the form of a fabric layer.

9. The knee brace of claim 8 wherein each of said releasably securable connectors comprises a multi-hook component of a releasable fastening system, and wherein said fabric layer of said outer surface is a plush fabric forming a cooperating component of said releasable fastening system, whereupon engagement of said multi-hook component to said plush fabric effects the releasable securement of said connector to said central portion of said brace.

10. The knee brace of claim 1 additionally comprising an opening on said longitudinal axis for receipt of the person's patella.

11. The knee brace of claim 10 wherein said brace has an inner surface and mounting means located on said inner surface of said brace adjacent said opening to releasably secure an optional component thereto.

12. The knee brace of claim 1 additionally comprising a pair of stays secured to said central portion on opposite sides of said longitudinal axis.

13. The knee brace of claim 1 wherein said brace has an inner surface and mounting means located on said inner surface of said brace to releasably secure an optional component thereto.

* * * * *